United States Patent [19]
Christidis et al.

[11] Patent Number: 5,550,286
[45] Date of Patent: Aug. 27, 1996

[54] PROCESS FOR THE PREPARATION OF AROMATIC CARBOXAMIDES FROM AROMATIC CARBOXYLIC ACIDS AND UREA

[75] Inventors: Yani Christidis, Paris, France; Michael Meier, Frankfurt, Germany

[73] Assignee: Hoechst AG., Germany

[21] Appl. No.: 354,206

[22] Filed: Dec. 12, 1994

[30] Foreign Application Priority Data

Dec. 14, 1993 [DE]  Germany ................. 43 42 571.2

[51] Int. Cl.$^6$ .................................. C07C 231/00
[52] U.S. Cl. ................ 564/139; 564/138; 564/140
[58] Field of Search ..................... 564/138, 139, 564/140

[56] References Cited

FOREIGN PATENT DOCUMENTS

| | | |
|---|---|---|
| 0869639 | 1/1953 | Germany . |
| 7235900 | 9/1972 | Japan ................................. 564/139 |
| 50-43531 | 4/1975 | Japan . |

OTHER PUBLICATIONS

Cherbuliez et al, Helv. Chimi. Acta, 29, 1438–46, 1946.
Egyptian Journal of Pharmaceutical Sciences, "*Study of Fusion of Urea with Some Aromatic Acids*" 'New Findings', vol. 13, No. 2, 231–235 (1972).
Chemical Abstracts, "*Benzonitriles*", Abstract No. 22297z of JP–A–06 032 758, vol. 103, No. 3, pp. 548 (Feb. 19, 1985).

*Primary Examiner*—Shailendra Kumar
*Attorney, Agent, or Firm*—Connolly & Hutz

[57] ABSTRACT

Process for the of aromatic carboxamides from aromatic carboxylic acids and urea Process for the preparation of aromatic carboxamides of the formula (I)

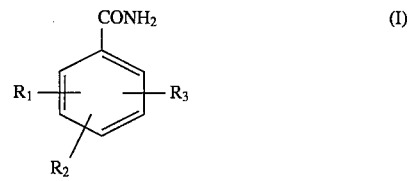

in which $R_1$, $R_2$, and $R_3$ are identical or different and are hydrogen, fluorine, chlorine or bromine atoms, or are alkyl($C_1$–$C_4$), hydroxyl or nitro groups, or $R_1$ and $R_2$ form an aromatic ring of 5 or 6 ring members, which ring may be substituted by fluorine, chlorine or bromine atoms or by alkyl($C_1$–$C_4$), hydroxyl or nitro groups, which involves reacting aromatic carboxylic acids of the formula (II)

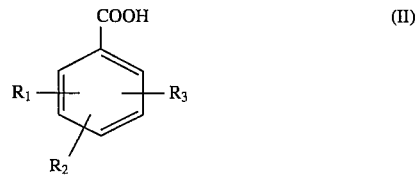

in which $R_1$, $R_2$ and $R_3$ are as defined above with urea in an inert organic solvent with the addition of a catalytic amount of phosphorous acid.

14 Claims, No Drawings

PROCESS FOR THE PREPARATION OF AROMATIC CARBOXAMIDES FROM AROMATIC CARBOXYLIC ACIDS AND UREA

DESCRIPTION

Process for the preparation of aromatic carboxamides from aromatic carboxylic acids and urea The invention relates to a process for the preparation of aromatic carboxamides from aromatic carboxylic acids and urea in an inert organic solvent with the addition of phosphorous acid.

Aromatic carboxamides are important intermediates for dyes, pigments, pharmaceuticals and plant protection agents.

The reaction of carboxylic acids with equimolar quantities of urea in the melt at 200°–230° C. to give the corresponding carboxamides is described in Helv. Chim. Acta 29, 1438–1446 (1946). In this reference benzamide is obtained in a yield of 60%.

DE 869 639 describes the preparation of 2-hydroxynaphthalene-3-carboxamide and salicylamide from the carboxylic acids using 4 mol of urea in the melt, with the addition of a catalytic quantity of phosphoric acid at from 170° to 180° C. in yields of 58% and 73% respectively.

The preparation of p-hydroxybenzamide from p-hydroxybenzoic acid and from 2 to 3 mol of urea in an inert organic solvent having a boiling point >160° C., preferably from 180° to 230° C., and with the addition of stoichiometric quantities of sulfamic acid is described in JP 5 043 531. Disadvantages of this process are the very high excess of urea and the use of stoichiometric quantities of sulfamic acid. The yield is 76.6%.

Also known is the reaction of aromatic carboxylic acids with slight excess of urea at from 200° to 220° C. This produces, in a crude yield of from 41 to 94%, the corresponding amides, which require recrystallization in order for a useful quality level to be attained (Chem. Listy 46, 306 (1952)).

A common feature of all the processes in the melt is that the carboxamides which are formed are strongly colored and heavily contaminated. By-products which are formed comprise up to about 25% of nitriles and up to 10% of the corresponding triazines (Egypt. J. Pharm. Sci. 13, 231 (1972)). In addition, the high solidification points of the melts make them difficult to handle technically.

There is therefore a great need for a process for the preparation of aromatic carboxamides from aromatic carboxylic acids, using urea, which is technically simple to carry out, avoids the abovementioned disadvantages and gives aromatic carboxamides not only in a high purity but also in a high yield.

This object is achieved by a process for the preparation of aromatic carboxamides of the formula (I)

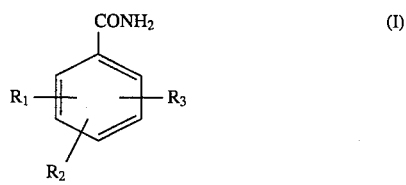

in which $R_1$, $R_2$, and $R_3$ are identical or different and are hydrogen, fluorine, chlorine or bromine atoms, or are alkyl($C_1$–$C_4$), hydroxyl or nitro groups, or $R_1$ and $R_2$ form an aromatic ring of 5 or 6 ring members, which ring may be substituted by fluorine, chlorine or bromine atoms or by alkyl($C_1$–$C_4$), hydroxyl or nitro groups.

The process comprises reacting aromatic carboxylic acids of the formula (II)

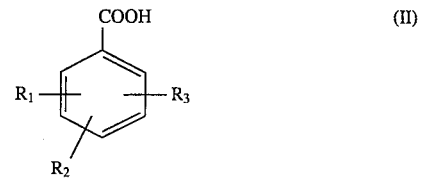

in which $R_1$, $R_2$ and $R_3$ are as defined above with urea in an inert organic solvent with the addition of a catalytic amount of phosphorous acid.

The process is particularly advantageous for the preparation of compounds of the formula (I) in which $R_1$, $R_2$ and $R_3$ are identical or different and are fluorine, chlorine or hydrogen atoms or nitro groups.

In the process according to the invention the inert organic solvent employed is an aromatic hydrocarbon, a chlorinated aromatic hydrocarbon or a mixture thereof. In many cases it has proven advantageous to use cumene, mesitylene, cymene, diisopropylnaphthalene, a chlorotoluene and/or dichlorobenzene in a proportion of from about 1 to 20 parts by weight, preferably from 2 to 5 parts by weight per part by weight of aromatic carboxamide. Instead of the pure solvent it is possible to employ the mother liquor from a preceding batch, without further purification. Larger quantities of solvent can of course also be used, although this reduces the space-time yield.

It has proven advantageous to employ for the reaction from 0.8 to 1.5 mol, in particular from 1.0 to 1.3 mol, of urea per mole of aromatic carboxamide.

It has been found advantageous to add phosphorous acid as catalyst in the reaction in quantities of from 0.01 to 5% by weight, preferably from 0.05 to 2% by weight.

In addition, it has been found useful to carry out the reaction at temperatures of from 140° to 200° C., in particular at temperatures of from 150° to 180° C.

The selectivity with regard to the carboxylic acid is generally greater than 98%, and the by-products described in the literature (Egypt. J. Pharm. Sci. 13, 231 (1972)) are almost completely absent. In accordance with the process of the invention, aromatic carboxamides are generally formed in high purity with yields of more than 80%. Unreacted carboxylic acid can be recovered and used again in a new batch. Instead of the pure solvent it is possible to use the mother liquor from a preceding batch, without purification, thus enabling the yield in many cases to be increased to about 95%.

The examples which follow serve to illustrate the process according to the invention without limiting it.

EXAMPLE 1

4-Nitrobenzamide 83.5 g (0.5 mol) of 4-nitrobenzoic acid, 33.0 g (0.55 mol) of urea and 0.5 g of phosphorous acid are heated in 250 ml of diisopropylnaphthalene with stirring at from 150° to 158° C. for 8 h. After cooling the batch to 25° C. the solid is filtered off with suction and washed with 50 ml of diisopropylnaphthalene. The filter cake is introduced into 250 ml of water, and the mixture is adjusted to a pH of 12 using aqueous sodium hydroxide solution and is stirred at 25° C. for 30 min. Subsequently the solid is filtered off with suction and dried at 100° C. 81.4 g of 4-nitrobenzamide are obtained having a melting point of from 191° to 194° C. This corresponds to a yield of 98% of theory.

EXAMPLE 2

4-Nitrobenzamide 83.5 g (0.5 mol) of 4-nitrobenzoic acid, 33.0 g (0.55 mol) of urea and 0.5 g of phosphorous acid are heated in 250 ml of o-chlorotoluene with stirring at from 150° to 157° C. for 8 h. After cooling to 25° C. the solid is filtered off with suction and washed with 50 ml of o-chlorotoluene. The filter cake is introduced into 250 ml of water, the mixture is adjusted to a pH of 12 using aqueous sodium hydroxide solution, and is subjected to steam distillation. Subsequently the solid is filtered off with suction and dried at 100° C. 74.9 g of 4-nitrobenzamide are obtained having a melting point of from 194 to 195° C. This corresponds to a yield of 90.3% of theory. By acidification of the aqueous mother liquor to pH 2, 3.4 g of 4-nitrobenzoic acid (4.1% of theory) are obtained which can be employed again in a subsequent batch.

EXAMPLE 3

4-Nitrobenzamide 83.5 g (0.5 mol) of 4-nitrobenzoic acid, 33.0 g (0.55 mol) of urea and 0.5 g of phosphorous acid are heated in 250 ml of cumene with stirring at 150° C. for 8 h. After cooling to 25° C. the solid is filtered off with suction and washed with 50 ml of cumene. The filter cake is introduced into 250 ml of water, the mixture is adjusted to a pH of 12 using aqueous sodium hydroxide solution, and is subjected to steam distillation. Subsequently the solid is filtered off with suction and dried at 100° C. 71.3 g of 4-nitrobenzamide are obtained having a melting point of from 192° to 193° C. This corresponds to a yield of 85.9% of theory. By acidification of the aqueous mother liquor to pH 2, 4.9 g of 4-nitrobenzoic acid (5.9% of theory) are obtained which can be employed again in a subsequent batch.

EXAMPLE 4

4-Nitrobenzamide 334 g (2.0 mol) of 4-nitrobenzoic acid, 120 g (2.0 mol) of urea and 2.0 g of phosphorous acid are heated in 1000 ml of mesitylene with stirring at from 158° C. to 163° C. for 8 h. After cooling to 25° C. the solid is filtered off with suction and washed with 200 ml of mesitylene. The filter cake is introduced into 1000 ml of water, the mixture is adjusted to a pH of 12 using aqueous sodium hydroxide solution, and is subjected to steam distillation. Subsequently the solid is filtered off with suction and dried at 100° C. 301.2 g of 4-nitrobenzamide are obtained, having a melting point of from 191° to 194° C. This corresponds to a yield of 90.7% of theory. By acidification of the aqueous mother liquor to pH 2, 12.5 g of 4-nitrobenzoic acid (3.7% of theory) are obtained which can be employed again in a subsequent batch.

334 g (2.0 mol) of 4-nitrobenzoic acid, 120 g (2.0 mol) of urea and 2.0 g of phosphorous acid are heated in 1000 ml of the organic mother liquor from the preceding experiment, with stirring, at from 158° to 163° C. The mixture is worked up as described above. 313.4 g of 4-nitrobenzamide are obtained having a melting point of from 192° to 195° C. This corresponds to a yield of 94.4% of theory. By acidification of the aqueous mother liquor to pH 2, 8.8 g of 4-nitrobenzoic acid (2.6% of theory) are obtained.

EXAMPLE 5

4-Chloro-3-nitrobenzamide 100 g (0.5 mol) of 4-chloro-3-nitrobenzoic acid, 36 g (0.6 mol) of urea and 0.5 g of phosphorous acid are heated in 250 ml of 1,2-dichlorobenzene with stirring at from 165° to 178° C. for 8 h. After cooling to 25° C. the solid is filtered off with suction and washed with 50 ml of 1,2-dichlorobenzene. The filter cake is introduced into 250 ml of water, and the mixture is adjusted to a pH of 12 using aqueous sodium hydroxide solution and subjected to steam distillation. Subsequently the solid is filtered off with suction and dried at 100° C. 89.7 g of 4-chloro-3-nitrobenzamide are obtained having a melting point of from 146° to 149° C. This corresponds to a yield of 90.2% of theory. By acidification of the aqueous mother liquor to pH 2, 4.9 g of 4-chloro-3-nitrobenzoic acid (4.9% of theory) are obtained, which can be employed again in a subsequent batch.

EXAMPLE 6

Benzamide 1.0 g (0.5 mol) of benzoic acid, 30.0 g (0.5 mol) of urea and 0.5 g of phosphorous acid are heated in 100 ml of mesitylene with stirring at from 150° to 158° C. for 8 h. After cooling to 25° C. the solid is filtered off with suction and washed with 30 ml of mesitylene. The filter cake is introduced into 100 ml of water and the mixture is adjusted to a pH of 12 with aqueous sodium hydroxide solution and subjected to steam distillation. Subsequently the solid is filtered off with suction and dried at 100° C. 51.1 g of benzoic acid are obtained having a melting point of from 122° to 125° C. This corresponds to a yield of 85.2% of theory.

EXAMPLE 7

4-Fluorobenzamide 70.0 g (0.5 mol) of 4-fluorobenzoic acid, 30.0 g (0.50 mol) of urea and 0.5 g of phosphorous acid are heated in 100 ml of mesitylene with stirring at from 150 to 158° C. for 8 h. After cooling to 25° C. the solid is filtered off with suction and is washed with 50 ml of mesitylene. The filter cake is introduced into 250 ml of water, and the mixture is adjusted to a pH of 12 with aqueous sodium hydroxide solution and subjected to steam distillation. Subsequently the solid is filtered off with suction and dried at 100° C. 50.7 g of 4-fluorobenzamide are obtained having a melting point of from 147° to 150° C. This corresponds to a yield of 72.9% of theory. By acidification of the aqueous mother liquor to a pH of 2, 5.9 g of 4-fluorobenzoic acid (8.4% of theory) are obtained, which can be employed again in a subsequent batch.

EXAMPLE 8

Isophthalamide 83.0 g (0.5 mol) of isophthalic acid, 60.0 g (1.0 mol) of urea and 0.5 g of phosphorous acid are heated in 250 ml of mesitylene with stirring at from 155° to 158° C. for 8 h. After cooling to 25° C. the solid is filtered off with suction and is washed with 50 ml of mesitylene. After conventional working up, 60.3 g of isophthalamide are obtained having a melting point of from 291° to 293° C. This corresponds to a yield of 73.5% of theory.

EXAMPLE 9

4-Nitrobenzamide (comparative example without phosphorous acid)

41.8 g (0.25 mol) of 4-nitrobenzoic acid and 15.0 g (0.25 mol) of urea are heated in 75 ml of mesitylene with stirring at from 158° to 163° C. for 8 h. After cooling to 25° C. the solid is filtered off with suction and washed with 25 ml of mesitylene. The filter cake is introduced into 100 ml of water, and the mixture is adjusted to a pH of 12 with aqueous sodium hydroxide solution and subjected to steam distillation. Subsequently the solid is filtered off with suction and dried at 100° C. 4.8 g of 4-nitrobenzoic acid are obtained having a melting point of from 191° to 194° C. This corresponds to a yield of 11.6% of theory.

EXAMPLE 10

4-Nitrobenzamide (comparative example with phosphoric acid)

83.5 g (0.50 mol) of 4-nitrobenzoic acid, 30.0 g (0.50 mol) of urea and 1 g of phosphoric acid are heated in 250 ml of mesitylene with stirring at from 160° to 162° C. for 8 h. After cooling to 25° C. the solid is filtered off with suction and is washed with 25 ml of mesitylene. The filter cake is introduced into 250 ml of water and the mixture is adjusted to a pH of 12 with aqueous sodium hydroxide solution and subjected to steam distillation. Subsequently the solid is filtered off with suction and is dried at 100° C. 52.0 g of 4-nitrobenzamide are obtained having a melting point of from 193° to 195° C. This corresponds to a yield of 62.7% of theory.

EXAMPLE 11

4-nitrobenzamide (comparative example with sulfamic acid)

83.5 g (0.50 mol) of 4-nitrobenzoic acid, 30.0 g (0.50 mol) of urea and 0.5 g of sulfamic acid are heated in 200 ml of dichlorobenzene with stirring at from 180° to 181° C. for 16 h. After cooling to 25° C. the solid is filtered off with suction and is washed with 50 ml of dichlorobenzene. The filter cake is introduced into 250 ml of water and the mixture is adjusted to a pH of 12 with aqueous sodium hydroxide solution and subjected to steam distillation. Subsequently the solid is filtered off with suction and is dried at 100° C. 40.6 g of 4-nitrobenzamide are obtained having a melting point of from 192° to 195° C. This corresponds to a yield of 48.9% of theory.

We claim:

1. A process for the preparation of an aromatic carboxamide of the formula (I)

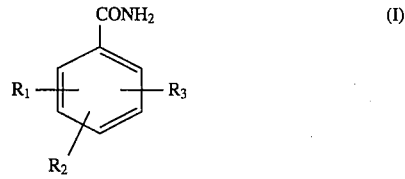

in which $R_1$, $R_2$, and $R_3$ are identical or different and are hydrogen, fluorine, chlorine or bromine atoms, or are alkyl ($C_1$–$C_4$), hydroxyl or nitro groups, or $R_1$ and $R_2$ form an aromatic ring of 5 or 6 ring members, which ring may be substituted by fluorine, chlorine or bromine atoms or by alkyl ($C_1$–$C_4$), hydroxyl or nitro groups, which comprises reacting an aromatic carboxylic acid of the formula (II)

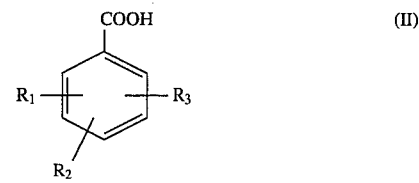

in which $R_1$, $R_2$ and $R_3$ are as defined above with urea in an inert organic solvent with the addition of a catalytic amount of phosphorous acid.

2. The process as claimed in claim 1, wherein $R_1$, $R_2$ and $R_3$ are identical or different and are fluorine, chlorine or hydrogen atoms or nitro groups.

3. The process as claimed in claim 1, which comprises employing as inert organic solvent an aromatic hydrocarbon, a chlorinated aromatic hydrocarbon or a mixture thereof.

4. The process as claimed in claim 1 which comprises employing as inert organic solvent cumene, mesitylene, cymene, diisopropylnaphthalene, a chlorotoluene and/or dichlorobenzene.

5. The process as claimed in claim 1, which comprises employing from 1 to 20 parts by weight solvent per part by weight of aromatic carboxylic acid.

6. The process as claimed in claim 1, which comprises employing from 0.8 to 1.5 mol, of urea per mole of aromatic carboxamide.

7. The process as claimed in claim 1, which comprises adding phosphorous acid as catalyst in the reaction in quantities of from 0.01 to 5% by weight.

8. The process as claimed in claim 1, which comprises carrying out the reaction at temperatures of from 140° to 200° C.

9. The process as claimed in claim 1, which comprises employing instead of the pure solvent the mother liquor from a preceding batch.

10. The process as claimed in claim 1, which comprises recovering unreacted carboxylic acid and recycling it to the reaction.

11. The process as claimed in claim 5, which comprises employing from 2 to 5 parts by weight of solvent per part by weight of aromatic carboxylic acid.

12. The process as claimed in claimed in claim 6, which comprises employing from 1.0 to 1.3 mol of urea per mole of aromatic carboxamide.

13. The process as claimed in claim 7, which comprises adding phosphorous acid as catalyst in the reaction in quantities of from 0.05 to 2% by weight.

14. The process as claimed in claim 8, which comprises carrying out the reaction at temperatures of from 150° to 170° C.

* * * * *